(12) United States Patent
Amann et al.

(10) Patent No.: US 7,008,105 B2
(45) Date of Patent: Mar. 7, 2006

(54) PATIENT SUPPORT DEVICE FOR RADIATION THERAPY

(75) Inventors: Karl Amann, Gebenbach (DE); Matthias Seufert, Oberreichenbach (DE); Jürgen Plannerer, Kemnath (DE)

(73) Assignee: Siemens Aktiengesellschaft, Munich (DE)

( * ) Notice: Subject to any disclaimer, the term of this patent is extended or adjusted under 35 U.S.C. 154(b) by 126 days.

(21) Appl. No.: 10/434,711

(22) Filed: May 9, 2003

(65) Prior Publication Data

US 2004/0028188 A1   Feb. 12, 2004

(30) Foreign Application Priority Data

May 13, 2002   (DE) .............................. 102 21 180

(51) Int. Cl.
    *A61B 6/04* (2006.01)
(52) U.S. Cl. ........................................ 378/209; 5/601
(58) Field of Classification Search ................. 5/600,
          5/601, 611; 108/22, 139, 141; 378/209;
          250/363.08
    See application file for complete search history.

(56) References Cited

U.S. PATENT DOCUMENTS

| | | | | |
|---|---|---|---|---|
| 4,501,414 A | * | 2/1985 | Mason et al. ................ | 378/209 |
| 4,669,136 A | * | 6/1987 | Waters et al. ................... | 5/601 |
| 4,771,785 A | * | 9/1988 | Duer ........................... | 600/415 |
| 4,833,972 A | * | 5/1989 | Bohusch et al. ................ | 5/600 |
| 4,885,998 A | * | 12/1989 | Span et al. .................. | 108/139 |
| 5,013,018 A | * | 5/1991 | Sicek et al. ..................... | 5/601 |
| 5,151,931 A | * | 9/1992 | Terashi et al. .............. | 378/209 |
| 5,160,337 A | * | 11/1992 | Cosman ...................... | 378/209 |
| 5,237,600 A | * | 8/1993 | Kamata ...................... | 378/209 |
| 6,416,219 B1 | * | 7/2002 | Pflaum et al. .............. | 378/209 |
| 6,456,684 B1 | * | 9/2002 | Mun et al. ................... | 378/209 |
| 6,502,261 B1 | * | 1/2003 | Harwood ....................... | 5/611 |
| 6,574,808 B1 | * | 6/2003 | Brown et al. .................. | 5/601 |
| 6,651,279 B1 | * | 11/2003 | Muthuvelan ................... | 5/600 |
| 6,721,976 B1 | * | 4/2004 | Schwaegerle ................. | 5/600 |

FOREIGN PATENT DOCUMENTS

| | | |
|---|---|---|
| CH | 678 451 A5 | 9/1991 |
| DE | OS 2046207 | 6/1971 |
| DE | 32 28 606 A1 | 3/1983 |
| DE | 38 03 567 A1 | 8/1989 |
| DE | 44 00 164 A1 | 7/1995 |
| DE | 44 29 813 C2 | 2/1998 |
| EP | 0 283 083 A1 | 3/1988 |
| EP | 1 362 617 A1 | 2/2003 |
| FR | 2 757 045 A-3 | 12/1996 |
| JP | 06000224 A | 1/1994 |
| WO | WO 88/01848 | 3/1988 |
| WO | WO02/32311 A1 | 4/2002 |

* cited by examiner

*Primary Examiner*—Michael Safavi
(74) *Attorney, Agent, or Firm*—Brinks Hofer Gilson & Lione

(57) ABSTRACT

A patient support device for a radiation therapy system has a load-bearing element, which is set up so as to be supported rotatably on a stationary structure about a vertical iso-axis extending through a treatment iso-center. The load-bearing element, with a patient tabletop mounted on it, can be leveled by a continuously adjustable leveling device. The leveling device is embodied in particular as a leveling shoe, which includes a bottom plate, a top plate, and an adjustable wedge disposed between them.

18 Claims, 3 Drawing Sheets

PATIENT SUPPORT DEVICE FOR RADIATION THERAPY

Figure 1:
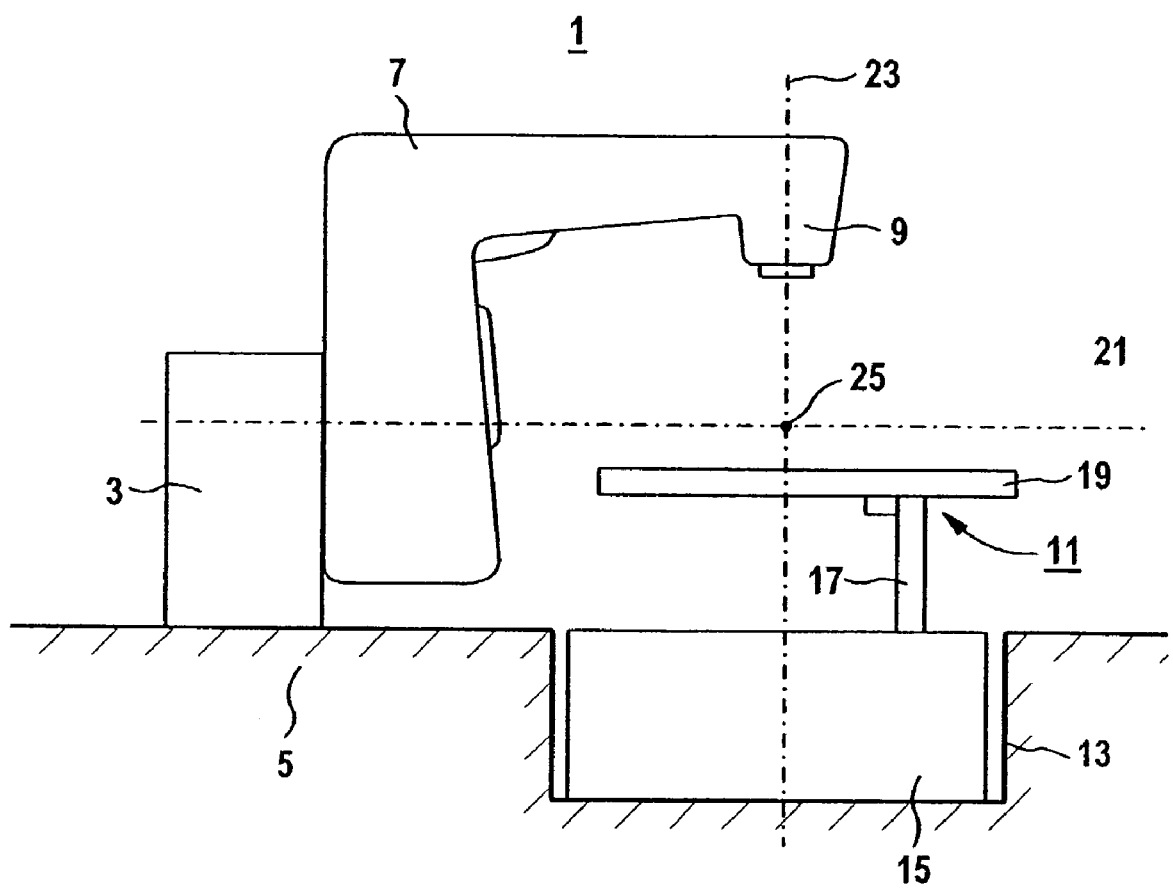

The invention relates to a patient support device for a radiation therapy system, having a load-bearing element, which is set up so as to be supported rotatably on a stationary structure about a vertical iso-axis extending through a treatment iso-center, and having a patient tabletop mounted on the load-bearing element.

German Patent Disclosure DE 38 03 567 A1 discloses a levelable patient support table that is not location-dependent or is moveable from place-to-place.

The invention is in the field of radiation therapy systems with which diseased tumor tissue, for instance, is treated by means of hard X-radiation, electrons, or gamma rays. Because of the high energy of the radiation employed for the purpose, which is lethal to the diseased tissue, the necessity exists of protecting body cells surrounding the diseased region. This is done by distributing the total dose over a plurality of irradiation angles. First, various irradiation angles are created by providing that the radiator head, during the irradiation, rotates about a horizontal axis (horizontal iso-axis), and the irradiation occurs either at discrete irradiation angles or continuously during the rotation. Second, various angles of incidence are created by rotating the patient tabletop about a vertical axis (vertical iso-axis). The two iso-axes intersect at a so-called treatment iso-center.

For irradiating a patient, the patient is placed horizontally on the patient tabletop, and then positioned laterally and vertically such that the diseased region to be irradiated comes to be located precisely in the iso-center. To enable performing this positioning exactly, the patient is as a rule marked beforehand in a simulator, and/or the tumor is located exactly beforehand using an imaging device. To achieve adequate positioning of the diseased tissue in the iso-center, the 3-D data obtained for instance in a computed tomography are also transmitted to the radiation therapy system, where they are used for patient positioning, or else the patient is oriented on the therapy system by means of markings made on the patient-for instance, using what is known as a "laser cross" (i.e., a projected cross-hair or target).

Since the gantry with the radiator head can pivot 360° about a horizontal axis, the patient cot or tabletop in the region of the iso-center must be fully accessible from below as well. The patient tabletop is, therefore as a rule, supported by a lifting column disposed eccentrically to the iso-center. For reasons of structural height, among others, a load-bearing element that supports the patient tabletop and is supported rotatably about the vertical iso-axis is as a rule mounted at least in part in a well or a tub in the floor. Radiation therapy systems or patient support devices of the above type have been described for instance in European Patent Disclosure EP 0 283 083 A1, German Published, not examined Patent Disclosure 20 46 207, and International Patent Disclosure WO 88/01848.

It is the object of the invention to increase the precision of irradiation in a radiation therapy system compared to known systems, so that the diseased tissue can be treated in a more target-specific manner, and finally also to achieve a radiation load or reduce a radiation dosage.

According to the invention, in terms of the patient support device defined at the outset, this object is attained by at least one continuously variable leveling device serving to orient the load-bearing element.

The invention is based on the recognition that for a radiation therapy system, very high precision in leveling the load-bearing element is especially critical. In particular, the load-bearing element must be leveled horizontally. In this way, above all exact patient positioning independently of the angular position of the iso-centric rotation, as well as a reduction in the forces of motion upon manual actuation of the rotation, are attained by avoiding skewing of the pivot axis except for a bare minimum. The invention is also based on the recognition that with modern radiation therapy systems, a degree of precision can be achieved for which a conventional rigid anchoring of the load-bearing element in the stationary structure no longer suffices. Until now, it was at most usual to provide only approximate leveling by utilizing metal underlay plates, or shims. The invention departs from this rigid anchoring that was usual until now and instead strikes a new course using continuously variable leveling.

Along with the advantage in terms of precision already mentioned, the advantage is also attained with the invention that installation is simplified and speeded up considerably, compared to the aforementioned procedure using metal shims.

In a preferred feature, the load-bearing element is set up so as to be mounted on the stationary structure directly or indirectly via the leveling device, preferably for nonstop or continuous operation. By leveling directly in the region of the bearing face, an especially simple construction is achieved.

It is also preferable that the leveling device is adjustable even after the installation of the load-bearing element on the stationary structure has been completed. Thus simple readjustment becomes possible without dismantling the patient support device, which is very heavy. The invention proceeds from the fact that with very precisely operating modern radiation therapy systems, such readjustment can become necessary over the course of time, in order to maintain the high precision.

In an especially preferred feature, the leveling is embodied as a leveling shoe. A leveling shoe of this kind for instance comprises a bottom plate, a top plate, and an adjustable wedge disposed between them.

Suitable leveling shoes that can be considered for this purpose are described for instance in German Patent DE 44 29 813 C2, German Patent Disclosures DE 44 00 164 A1 and DE 32 28 606 A1, or Swiss Patent Disclosure CH 678 451 A5. The leveling shoe of DE 44 29 813 C2 includes a bottom plate, a top plate, and a wedge disposed between them, which can be inserted more or less deeply in between the bottom plate and the top plate via a horizontal spindle supported rotatably and axially nondisplaceably in it; an anchoring member engaging between the bottom plate and the top plate, which is freely displaceable vertically relative to them but fixed in them in the direction of the spindle, is screwed to the spindle, thereby making the perpendicular spacing of the bottom plate and the top plate variable.

Preferably, the leveling device in the patient support device is disposed such that a horizontal motion of the wedge causes a vertical motion of the load-bearing element.

Preferably, the leveling device has a horizontally supported spindle for adjusting the wedge, which in particular points substantially in the direction of the vertical iso-axis.

In an especially preferred feature, the patient support device has at least three, and in particular precisely three, leveling devices. The invention is in fact based on the recognition that-contrary to what until now was the usual procedure in which for leveling, fastening bores and optionally metal plates acting as shims were provided at sixteen points-a three-point support is possible for a radiation therapy system despite the great weight of a patient support device. This is also based in particular on the recognition that the leveling shoes already mentioned, because of their load-bearing capacity, are adequate for this kind of three-point support. Because the components for the vertical iso-centric rotation are secured now at only three points, it is advantageously possible to dispense with a stable metal tub in the floor that has a fastening flange machined over a large area. In the simplest case, all that has to be done is to adjust, i.e. tighten or loosen three screws.

The load-bearing element can be mounted at least in part in a well in the floor functioning as a stationary structure. However, a support column for a gantry, or the gantry itself, can also be considered for the stationary structures.

Particularly in conjunction with the aforementioned three-point support, it is expedient that the well in the floor, on its bottom face, has a mounting face of concrete, in which the leveling device is anchored directly. The anchoring can be achieved for instance with special dowels in the concrete floor; in particular, one dowel per leveling shoe would be sufficient.

The load-bearing element can be connected to the patient tabletop via a lifting column mounted preferably outside the vertical iso-axis.

To assure mobility of the radiator head by 360° about the horizontal iso-axis, it is expedient that the load-bearing element has a cantilevered arm for receiving the lifting column.

The patient tabletop can be positioned or positionable such that it is penetrated by the vertical iso-axis at one point.

A radiation therapy system with a patient support device according to the invention is also within the scope of the invention. For the advantages and preferred versions in this respect, see those pertaining to the patient support device above.

Figure 2:
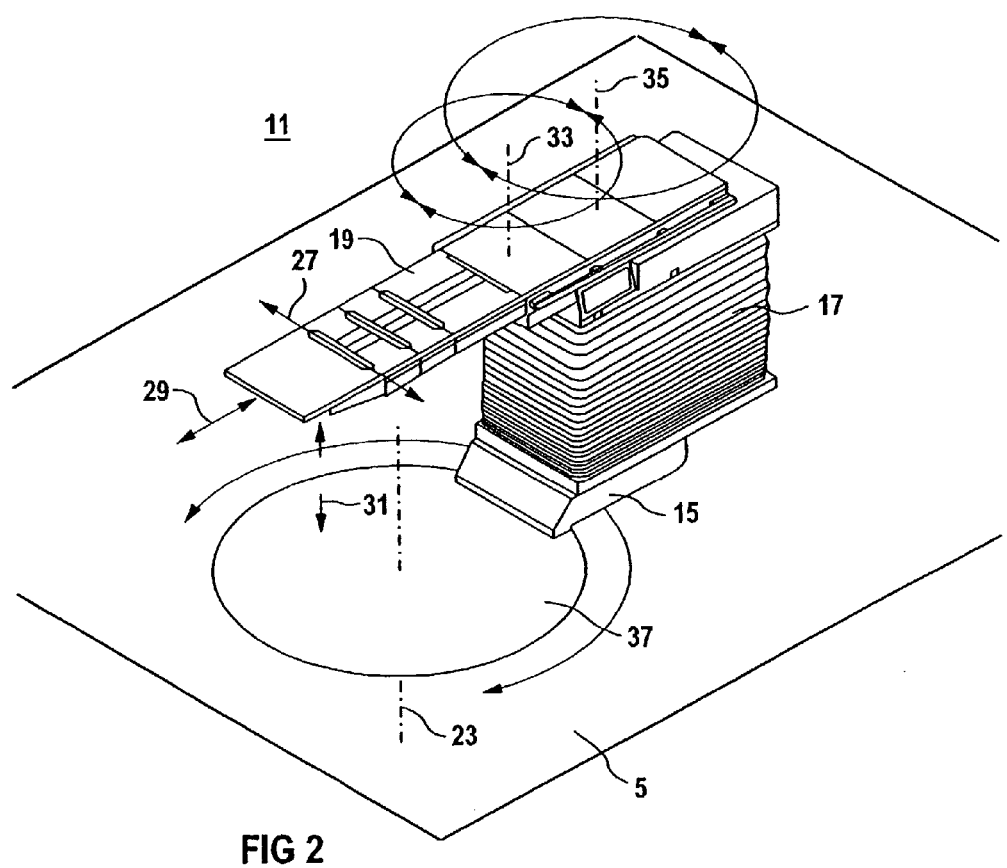
Figure 3:
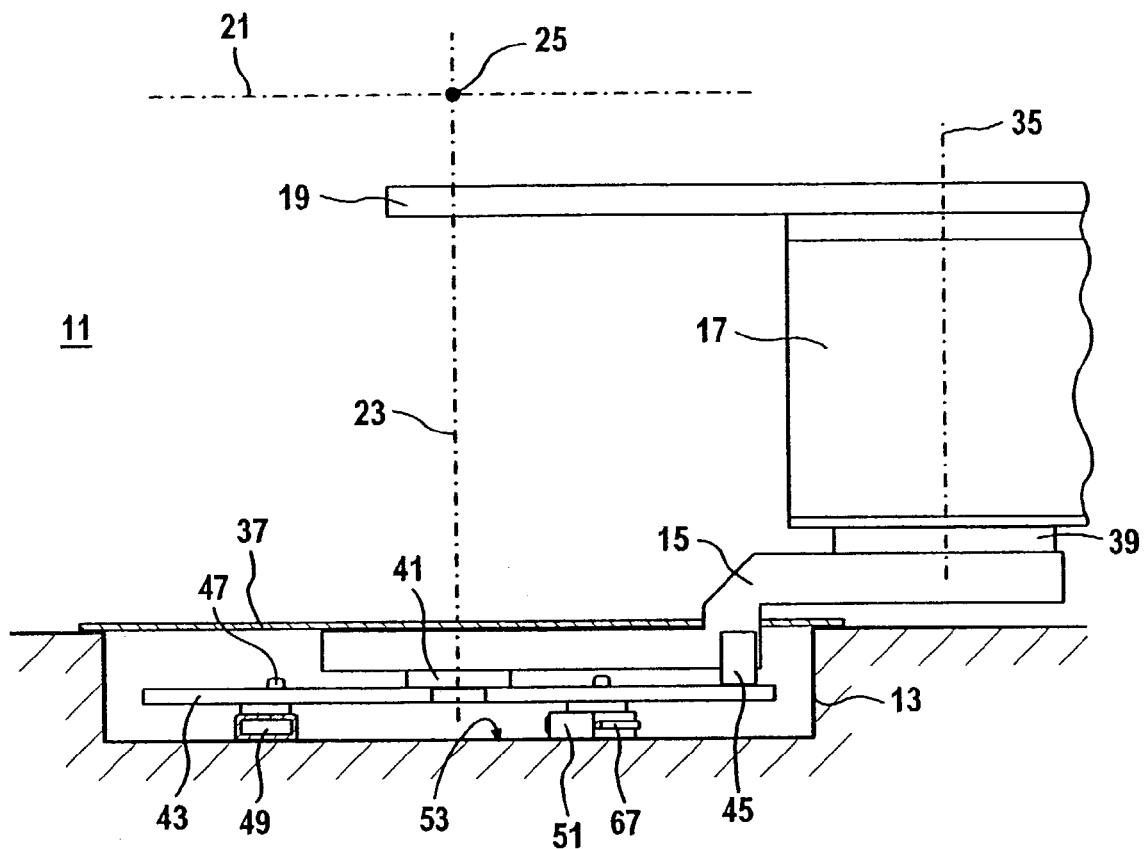

Exemplary embodiments of a patient support device and a radiation therapy system according to the invention will be described in further detail below in conjunction with FIGS. 1–4. Shown are:

FIG. 1, a schematic overall view of a radiation therapy system of the invention;

FIG. 2, a perspective view of a detail of the patient support device of the radiation therapy system of FIG. 1;

FIG. 3, a cross-sectional view of the patient support device of FIG. 2; and

Figure 4:
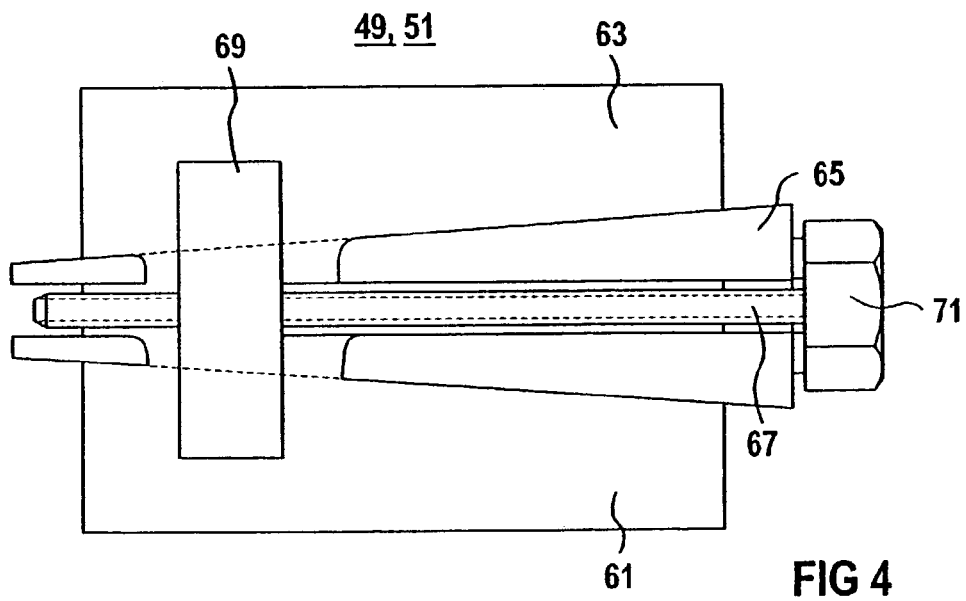

FIG. 4, a schematic illustration of a leveling used to adjust the patient support device of FIGS. 2 and 3.

FIG. 1 shows a radiation therapy system, identified overall by reference numeral 1. The radiation therapy system 1 includes a floor-mounted column 3, which is secured to a floor 5 of an examination room or building. A gantry 7, stand or frame is rotatably supported on the floor-mounted column 3 and on one end has a radiation source 9, such as an X-ray source or a gamma-ray source.

The radiation therapy system 1 also includes a patient support device 11. The patient support device is supported rotatably in a well 13 in the floor via a load-bearing element 15. Via a lifting column 17, a patient tabletop 19 for a patient, not explicitly shown, to be placed on is mounted on the load-bearing element 15.

The gantry 7 with the radiation source 9 is rotatable about a horizontal iso-axis 21, and the patient support device 11 and in particular the patient tabletop 19 is rotatable about a vertical iso-axis 23. The rotation about the vertical iso-axis 23 allows more different irradiation angles in space to be attained than would be possible if the gantry were rotated only about the horizontal iso-axis 21.

The two iso-axes 21, 23 are oriented in such a way that they intersect at a common treatment iso-center 25.

In this treatment iso-center 25, the patient placed on the patient tabletop 19, for instance a patient with a tumor to be treated, is positioned.

As shown in detail in FIG. 2, to this end, translational motions of the patient tabletop 19 in a lateral direction 27 and a longitudinal direction 29, both of which are in the horizontal plane, are possible. A lifting height adjustment in the vertical direction 31 is also possible with the lifting column 17. The lifting column guarantees a wide range of adjustment, for instance to position the patient far away from the radiator head for the sake of utilizing a maximum field size, since the beam is divergent.

Since the gantry 7 is pivotable by 360° about the horizontal iso-axis 21, the tabletop 19 in the region of the iso-center 25 is also fully accessible from below, which is why the lifting column 17 is disposed eccentrically.

In FIG. 2, two axes of rotation can also be seen: The patient tabletop 19 is pivotable by ±180° on the lifting column 17 about a first vertical axis 33. The lifting column 17 is in turn pivotable by ±180° about a second vertical axis 35.

The possibilities of rotation about the vertical axes 33, 35 allow parallel shifting of the patient tabletop 19, so that a patient can be treated if needed in a hospital bed. In addition, by a combined motion about both axes, the lateral range of adjustment of the tabletop 19 can be expanded.

It can also be seen in FIG. 2 that the load-bearing element 15 protrudes with a cantilevered arm part out of the floor well 13 that is otherwise covered by a cover plate 37 that can rotate with the load-bearing element 15. The cover plate 37 is removable, so that the construction elements located below it and shown in further detail in FIG. 3 can be reached.

In FIG. 3, it can be seen in detail that the lifting column 17 is supported, via a column rotation bearing 39, on the cantilevered arm-like part of the load-bearing element 15 that protrudes past the floor well 13 or tub. The armlike load-bearing element 15 is in turn supported via a base bearing 41 on a base plate 43 rotatably about the vertical iso-axis 23. The rotation about this axis is assured by a motor driven support roller 45, which supports the load-bearing element 15 and can be rolled along a circular path on the base plate 43.

The base plate 43 is connected via fastening screws 47 to a total of three leveling means 49, 51, disposed at equidistant azimuthal spacing about the vertical iso-axis 23, which in turn are mounted on a concrete mounting face 53 of the floor well 13. Because of the three support points, the support or bearing is statically defined. The three-point support makes mounting, installing or assembly possible in a way that saves both time and expense. The leveling means 49, 51, embodied as leveling shoes or machine shoes, are anchored via special dowels directly in the concrete floor. It is not necessary for the floor well 13 to be lined with metal.

FIG. 4 shows as an example and schematically one possible leveling 49, 51. This leveling has a bottom plate 61, a top plate 63, and a wedge 65 disposed between them, which can be inserted more or less deeply between the bottom plate 61 and top plate 63 by utilizing a horizontal screw or a threaded spindle 67 supported rotatably and axially nondisplaceably in it, thereby making the vertical spacing of the bottom plate 61 from the top plate 63 variable. An anchoring member 69, which engages the bottom plate 61 and the top plate 63, is freely displaceable vertically relative to them, and is fixed in them in the direction of the spindle 67, is screwed onto the spindle 67. The spindle 67 can be driven manually from outside via a screw head 71.

The leveling devices 49, 51 (see FIG. 3) are disposed such that by utilizing a horizontal motion of the wedge 65, a vertical motion of the load-bearing element 15 is brought about. In particular, the spindle 67 is supported horizontally and disposed radially relative to the vertical iso-axis 23 so that the screw head 71 is easily accessible to service technicians from outside once the cover plate 37 has been removed.

Because of the use of the leveling devices 49, 51, the iso-centric rotation of the therapy tabletop can be leveled at any time without reinstallation. If a fine-thread spindle is used, a very slight adjusting torque and thus very precise leveling are attainable. Only a compact tool is needed, which the service technicians can easily introduce into the floor well 13 without being hindered in moving about.

For retrofitting existing floor tubs with metal linings, sheet-metal adapters can be inserted, being placed in particular between the leveling elements 49, 51 and the metal region of the floor tub.

What is claimed is:

1. A patient support device for a radiation therapy system comprising:
    a load-bearing element supported rotatably on a stationary floor of a well structure about a vertical iso-axis extending through a treatment iso-center; and
    a patient tabletop mounted on the load-bearing element, wherein at least one continuously variable leveling device serves to orient the load-bearing element,
    wherein the at least one continuously variable leveling device includes a bottom plate, a top plate, and an adjustable wedge disposed between the bottom and top plates, and
    wherein the at least one continuously variable leveling device is disposed such that a horizontal motion of the adjustable wedge causes a vertical motion of the load-bearing element.

2. The patient support device as in claim 1, wherein the load-bearing element is mounted on the stationary floor of the well structure directly or indirectly via at least one leveling device.

3. The patient support device as in claim 1, wherein the at least one continuously variable leveling device remains adjustable after the installation of the load-bearing element on the stationary structure.

4. The patient support device as in claim 1, wherein the at least one continuously variable leveling device comprises a leveling shoe.

5. The patient support device as in claim 1, wherein the load-bearing element is connected to the patient tabletop via a lifting column mounted.

6. The patient support device as in claim 5 wherein the lifting column is mounted outside the vertical iso-axis.

7. The patient support device as in claim 5, wherein the load-bearing element has a cantilevered arm for receiving the lifting column.

8. The patient support device as in claim 1, wherein the patient tabletop is positioned such that it is penetrated by the vertical iso-axis at one point.

9. The patient support device as in claim 1, wherein at least three leveling devices are present.

10. The patient support device as in claim 9, wherein precisely three levelings are present.

11. The patient support device as in claim 2 wherein the at least one continuously variable leveling device remains adjustable after the installation of the load-bearing element on the stationary floor of the well structure and comprises a leveling shoe including a bottom plate, a top plate, and the adjustable wedge is disposed between the bottom and top plates, wherein the at least one continuously variable leveling device also has a horizontally supported threaded spindle for adjusting the wedge, the spindle pointing substantially in the direction of the vertical iso-axis.

12. The patient support device as in claim 1, wherein the load-bearing element is mounted at least in part in the floor well functioning as the stationary structure.

13. The patient support device as in claim 1, wherein the load-bearing element is mounted at least in part in the floor well functioning as the stationary structure, and wherein the load-bearing element is connected to the patient tabletop via a lifting column mounted preferably outside the vertical iso-axis.

14. The patient support device as in claim 1, wherein the load-bearing element is connected to the patient tabletop via a lifting column and wherein the patient tabletop is positioned such that it is penetrated by the vertical iso-axis at one point.

15. A patient support device for a radiation therapy system comprising:
    a load-bearing element supported rotatably on a stationary floor of a well structure about a vertical iso-axis extending through a treatment iso-center; and
    a patient tabletop mounted on the load-bearing element, wherein at least one continuously variable leveling device serves to orient the load-bearing element,
    wherein the at least one continuously variable leveling device includes a bottom plate, a top plate, and an adjustable wedge disposed between the bottom and top plates, and
    wherein the at least one continuously variable leveling device has a horizontally supported threaded spindle for adjusting the wedge.

16. The patient support device as in claim 15, wherein the spindle points substantially in the direction of the vertical iso-axis.

17. A patient support device for a radiation therapy system comprising:
    a load-bearing element supported rotatably on a stationary floor of a well structure about a vertical iso-axis extending through a treatment iso-center; and
    a patient tabletop mounted on the load-bearing element;
    wherein at least one continuously variable leveling device serves to orient the load-bearing element, and
    wherein the load-bearing element is mounted at least in part in the floor well functioning as the stationary structure, and the floor well on its bottom face, has a mounting face of concrete, in which levelings are anchored directly.

18. A patient support device for a radiation therapy system comprising:
    a load-bearing element supported rotatably on a stationary floor of a well structure about a vertical iso-axis extending through a treatment iso-center; and
    a patient tabletop mounted on the load-bearing element;
    wherein at least one continuously variable leveling device serves to orient the load-bearing element, and
    wherein the load-bearing element is mounted at least in part in the floor well functioning as the stationary structure, wherein the at least one continuously variable leveling device includes a bottom plate, a top plate, and an adjustable wedge disposed between the bottom and top plates.

* * * * *